United States Patent [19]
Babinski et al.

[11] Patent Number: 6,024,951
[45] Date of Patent: Feb. 15, 2000

[54] SOAP-FREE SHAVE LOTION THAT INCREASES SURFACE ADHERENCE AND RELATED METHODS

[75] Inventors: Linda J. Babinski, Somers; James A. Limburg, Wind Point, both of Wis.

[73] Assignee: S. C. Johnson & Son, Inc., Racine, Wis.

[21] Appl. No.: 09/042,027

[22] Filed: Mar. 13, 1998

[51] Int. Cl.$^7$ ....................................................... A61K 7/15
[52] U.S. Cl. ............................ 424/73; 424/70.1; 424/401
[58] Field of Search ................................ 424/73, 401, 70.1

[56] References Cited

U.S. PATENT DOCUMENTS

| | | | |
|---|---|---|---|
| 4,892,729 | 1/1990 | Cavazza | 424/73 |
| 5,192,462 | 3/1993 | Gloor et al. | 554/227 |
| 5,439,682 | 8/1995 | Wivell et al. | 724/401 |
| 5,575,990 | 11/1996 | Benfatto | 424/65 |
| 5,610,125 | 3/1997 | Zimmerman | 510/123 |
| 5,641,479 | 6/1997 | Linares et al. | 424/401 |
| 5,672,576 | 9/1997 | Behrens et al. | 510/127 |
| 5,674,511 | 10/1997 | Kacher et al. | 424/401 |

Primary Examiner—James M. Spear

[57] ABSTRACT

A soap-free, non-lathering shaving preparation that increases surface adherence ability when applied to the skin, a method for shaving using the shaving preparation, and a method for increasing the surface adherence ability of a soap-free, non-lathering shaving preparation. In one aspect, the shaving preparation composition includes ethoxylated fatty ester, in an amount between about 0.01 and about 1 weight percent of the composition, for increasing the surface adherence ability of the shaving preparation; behenylquaternary surfactant, in an amount between about 0.25 and about 7.5 weight percent of the composition; fatty alcohol, in an amount between about 0.75 and about 22.5 weight percent of the composition; and water, in an amount between about 40 and about 90 weight percent of the composition. In another aspect, a method of shaving comprises applying the shaving preparation to a surface to be shaved, and shaving the surface with a razor. In yet another aspect, a method for increasing the surface adherence ability of a soap-free, non-lathering shaving preparation comprises adding ethoxylated fatty ester to the shaving preparation to produce a shaving preparation having a rinse off value of at least about 60 seconds.

42 Claims, No Drawings

SOAP-FREE SHAVE LOTION THAT INCREASES SURFACE ADHERENCE AND RELATED METHODS

BACKGROUND OF THE INVENTION

1. Field of the Invention

The present invention relates to a soap-free, non-lathering shave lotion, and more particularly, to an improved soap-free, non-lathering shave lotion that increases surface adherence. This invention also relates to methods for shaving using this improved formulation, and a method for increasing the surface adherence ability of a soap-free, non-lathering shave lotion.

2. Related Art

Shaving preparations have long been available as powders, creams, and foams formulated to exhibit excellent lathering ability. More recently, consumers have been introduced to gel shaving compositions, which can be worked into a lather when rubbed against the skin.

Shaving preparations generally include soap as a major component. As used herein, "soap" means a salt of a fatty acid with a base. Examples are the salts of fatty acids with ammonia, low molecular weight amines (especially alkanolamines), and alkali metals (especially sodium and potassium). Other fatty acid salts result from the reaction of metallic cations (e.g., zinc, aluminum, and alkaline earth metals such as calcium and magnesium) with long chain fatty amines. The most common soaps used in shaving preparations are stearates and palmitates.

A drawback to using soap, however, lies in its tendency to cause irritation to the skin, particularly to delicate and broken skin, during shaving. Soap-containing shaving preparations can also cause drying of the skin and premature dulling of razor blades.

Accordingly, in recent years, the cosmetics industry has developed soap-free, non-lathering shaving preparations, as discussed, for example, in U.S. Pat. No. 4,892,729 (hereby incorporated by reference in its entirety), to overcome the above-described drawbacks of soap-based formulations. By non-lathering, we mean shaving preparations that do not contain surfactants of the lathering or foaming type, as understood by one of ordinary skill in the art.

Soap-free, non-lathering shaving preparations have found popular application as shaving lotions for use in the shower. Unfortunately, currently available shaving lotions are easily rinsed from the surface of the skin. This can make shaving of body parts difficult, if not impossible, in the shower.

Our invention is directed to improving the skin adhering ability of soap-free, non-lathering shaving preparations. We have found that adding certain ethoxylated fatty esters to a behenylquaternary surfactant-based composition produces a shave lotion that exhibits superior increased surface adherence when applied to the skin. As used herein, "surface adherence" refers to the ability of a substance to adhere to a surface and resist rinsing, and can be measured quantitatively by the amount of time it takes to rinse away completely the substance from the surface.

Ethoxylated fatty esters (otherwise known as polyether esters) have found application in cosmetic compositions as thickening agents for shampoos, conditioners, skin lotions, facial creams, and the like, as discussed in U.S. Pat. No. 5,192,462; U.S. Pat. No. 5,641,479; U.S. Pat. No. 5,610,125; U.S. Pat. No. 5,674,511; U.S. Pat. No. 5,439,682; U.S. Pat. No. 5,672,576; U.S. Pat. No. 5,575,990; and U.S. Pat. No. 5,389,305. However, none of these patents teaches or suggests the use of ethoxylated fatty esters to increase the surface adherence of a composition after application to the skin.

In short, there exists a need for a soap-free, non-lathering shaving preparation exhibiting increased surface adherence.

SUMMARY OF THE INVENTION

An object of this invention is to provide a soap-free, non-lathering shaving preparation having increased skin adhering and rinse resistance abilities. We have found that adding certain ethoxylated fatty esters to a behenylquaternary surfactant-based composition produces a lotion shave preparation that exhibits unexpected and superior surface adherence when applied to the skin.

In one aspect of our invention, a shaving preparation comprises ethoxylated fatty ester, in an amount between about 0.01 and about 1 weight percent of the composition, for increasing the surface adherence of the composition, the ethoxylated fatty ester having the formula:

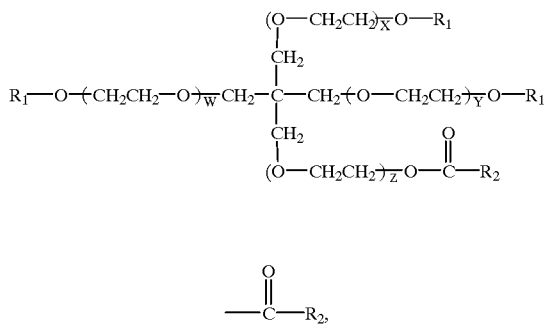

$R_2$ is a hydrocarbon chain having greater than 5 carbon atoms, and (W+X+Y+Z) is greater than 60; behenylquaternary surfactant, in an amount between about 0.25 and about 7.5 weight percent of the composition; fatty alcohol, in an amount between about 0.75 and about 22.5 weight percent of the composition; and water, in an amount between about 40 and about 90 weight percent of the composition. The shaving preparation may further include PEG 6 capric/caprylic triglycerides, in an amount between about 0.01 and about 1 weight percent of the composition.

In another aspect, the ethoxylated fatty ester comprises PEG 150 distearate, in an amount between about 0.01 and about 2 weight percent of the composition. In yet another aspect, the ethoxylated fatty ester comprises PEG 6 capric/caprylic triglycerides, in an amount between about 0.01 and about 1 weight percent of the composition. As used herein, "PEG" means "polyethylene glycol."

Another object of this invention is to provide a method for shaving using our novel compositions. In one aspect, the method generally comprises applying a shaving preparation having a composition of our invention to a surface to be shaved, and shaving the surface with a razor.

Another object of our invention is to provide a method for increasing the surface adherence ability of a soap-free, non-lathering shaving preparation. In one aspect, the method generally comprises adding certain ethoxylated fatty ester compounds to a shaving preparation comprising behenylquaternary surfactant, fatty alcohol, and water. The resulting shaving preparation has a composition in accordance with our invention, and has a rinse off value of at least about 60 seconds.

Other aspects of the invention will be better understood and advantages thereof more apparent in view of the following detailed description of the preferred embodiments.

DETAILED DESCRIPTION OF THE PREFERRED EMBODIMENTS

Main components of the shaving preparation of this invention include ethoxylated fatty ester; behenylquaternary surfactant; fatty alcohol; and water. Additional components can include organo-substituted polysiloxane; emollients; pigments; plastic particles; and common shaving preparation and cosmetic additives.

The ethoxylated fatty ester preferably comprises, either alone or in any combination with the other ethoxylated fatty esters set forth below, (i) a compound having the following Formula (1):

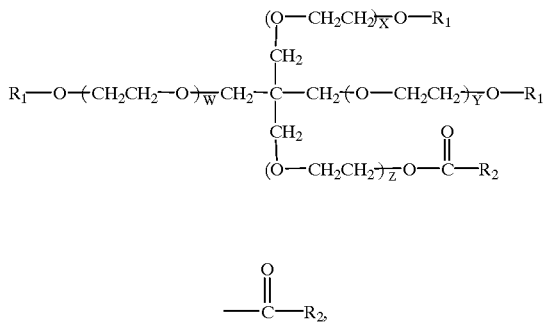

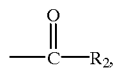

$R_2$ is a hydrocarbon chain having greater than 5 carbon atoms, and (W+X+Y+Z) is greater than 60;

(ii) PEG 150 distearate, or (iii) PEG 6 capric/caprylic triglycerides.

As used herein, "PEG" means "polyethylene glycol." It is believed that PEG esters in general, having between 2 and 5 fatty acid tails, are equivalent ethoxylated fatty esters for practicing our invention.

The ethoxylated fatty ester of Formula (1) comprises preferably between about 0.01 and about 1 weight percent of the composition, more preferably between about 0.01 and about 0.5 weight percent of the composition, and most preferably between about 0.1 and about 0.2 weight percent of the composition.

We have found that a preferred ethoxylated fatty ester of compound (i) is PEG 150 pentaerythrityl tetrastearate. A preferred source of PEG 150 pentaerythrityl tetrastearate is CROTHIX liquid (from Croda Inc. of Parsippany, N.J.), which contains 45% PEG 150 pentaerythrityl tetrastearate.

PEG 150 distearate comprises preferably between about 0.01 and about 2 weight percent of the composition, more preferably between about 0.05 and about 0.5 weight percent of the composition, and most preferably between about 0.1 and about 0.3 weight percent of the composition.

PEG 6 capric/caprylic triglycerides comprises preferably between about 0.01 and 1 weight percent of the composition, more preferably between about 0.01 and about 0.5 weight percent of the composition, and most preferably between about 0.05 and about 0.15 weight percent of the composition. Preferred sources are Glycerox 767 (from Croda, Inc.) and CROTHIX liquid (from Croda Inc.), which contains 25% PEG 6 capric/caprylic triglycerides.

In a preferred form, our shaving preparation includes both the ethoxylated fatty ester of compound (i) and PEG 6 capric/caprylic triglycerides. When used in combination, the ethoxylated fatty ester of compound (i) comprises preferably between about 0.01 and about 1 weight percent of the composition, more preferably between about 0.01 and about 0.5 weight percent of the composition, and most preferably between about 0.1 and about 0.2 weight percent of the composition; the PEG 6 capric/caprylic triglycerides comprises preferably between about 0.01 and about 1 weight percent of the composition, more preferably between about 0.05 and about 0.5 weight percent of the composition, and most preferably between about 0.05 and about 0.15 weight percent. Furthermore, it is preferable that the combined amounts of ethoxylated fatty ester of compound (i) and PEG 6 capric/caprylic triglycerides be at most about 1.5 weight percent of the composition.

The behenylquaternary surfactant comprises preferably between about 0.25 and about 7.5 weight percent of the composition, more preferably between about 0.75 and about 2 weight percent of the composition, and most preferably between about 1.25 and about 1.75 weight percent of the composition. The behenyl quaternary surfactant is preferably behentrimonium methosulfate or behentrimonium chloride. A preferred source of behentrimonium methosulfate is INCROQUAT Behenyl TMS (from Croda Inc.), which comprises 25% behentrimonium methosulfate. Alternatively, the surfactant may be behenalkonium chloride, dibehenyldimonium methosulfate, or behenamidopropyl ethyldimonium ethosulfate.

Fatty alcohol comprises preferably between about 0.75 and about 22.5 weight percent of the composition, more preferably between about 2.25 and about 6 weight percent of the composition, and most preferably between about 3.75 and about 5.25 weight percent of the composition. A preferred fatty alcohol is cetearyl alcohol. A preferred source of cetearyl alcohol is INCROQUAT Behenyl TMS, which contains 75% cetearyl alcohol.

Water comprises preferably between about 40 and about 90 weight percent of the composition, more preferably between about 70 and about 80 weight percent of the composition, and most preferably between about 75 and about 80 weight percent of the composition.

Organo-substituted polysiloxanes, also known as silicones, are linear or cyclic polymers of monomeric silicon/oxygen monomers. The polymeric backbone of silicon is made up of alternating silicon and oxygen atoms. The silicon atoms may carry a wide variety of substituents which can be the same or different. Most often, methyl and phenyl groups are used. However, other alkyl and aryl substitutes can be included. We have found the preferred silicone to be dimethicone, due to its skin protectant properties. Dimethicone has a preferred viscosity grade of about 50 centistokes.

Organo-substituted polysiloxanes preferably comprise up to about 20 weight percent of the composition, more preferably between about 3 and about 10 weight percent of the composition, and most preferably between about 6 and about 8 weight percent of the composition.

The preferred range of emollients is between about 0.1 and about 20 weight percent of the composition. Preferred emollients include mineral oil and isopropyl palmitate. Each of the mineral oil and isopropyl palmitate comprises preferably between about 1 and about 10 weight percent of the composition, more preferably between about 1 and about 5 weight percent of the composition, and most preferably between about 1 and about 3 weight percent of the composition. Various other emollients are also suitable, such as petrolatum, fatty esters, other fatty alcohols, glycerides, amino acids, lanolin, lanolin derivatives, vegetable oils, polyols, and other silicone derivatives.

To improve trackability (the ability of a consumer to see which areas have been shaved and which have not), it is desirable to add a pigment. A preferred pigment is titanium dioxide ($TiO_2$). Titanium dioxide comprises preferably between about 0.05 and about 5 weight percent of the composition, more preferably between about 1 and about 2 weight percent of the composition, and most preferably about 1.5 weight percent of the composition. Of course, equivalent pigments may be used as desired.

The composition of our invention may also include plastic particles, such as beads, in an amount between about 0.1 and about 20 weight percent of the composition, more preferably between about 1 and about 10 weight percent of the composition, and most preferably between about 2 and about 5 weight percent of the composition. The addition of plastic particles helps loosen dead skin for removal during shaving. Preferred plastic particles include oxidized polyethylene beads, which can be a mixture of Acumist A45 beads, average particle size of about 45 μm (from Allied Signal of Morristown, N.J.); 316A beads, average particle size of about 141 μm (from Allied Signal); and 9F beads, average particle size of about 110 μm (from Allied Signal).

Other common shaving preparation and cosmetic additives can be used in our invention, including, but not limited to, vitamin E acetate USP, aloe vera powder, fragrances, colorants, and preservatives, such as methylparaben, propylparaben, and GERMABEN II-E (diazolidinyl urea and parabens preservative).

Shaving preparations of the present invention can be made, generally, by first heating about 60 percent of the water to about 165–175° F., then adding the behenyl quaternary surfactant and the ethoxylated fatty ester, and mixing well. Next, the organo-substituted polysiloxanes and emollients are added and mixed well, followed by mixing in of the pigments and the plastic particles. After that, the remaining water is added, mixed well, and cooled to about 100° F. Other common shaving preparation and cosmetic additives, such as vitamin E acetate USP, aloe vera powder, fragrances, colorants, and preservatives, are then added as desired.

In a preferred form, the shaving preparation of our invention is essentially free of soap. By essentially free of soap, we mean our preparations include only those unavoidable trace impurities of soap contained in the starting materials or components.

In another preferred form, our shaving preparation has a rinse off value of at least about 60 seconds, as measured by the "Rinse Testing Procedure" set forth below in the Comparative Testing section.

Our invention also includes a method of shaving a surface, such as human skin having hair projecting therefrom. A preferred method includes applying a shaving preparation composition of this invention to a surface to be shaved, and then shaving the surface with a razor. Another preferred method includes wetting a surface to be shaved, applying a shaving preparation composition of this invention to the surface, and shaving the surface with a razor.

In one embodiment of our invention, our method of shaving comprises applying a shaving preparation composition comprising: (i) ethoxylated fatty ester, in the form of Formula (1) in an amount between about 0.01 and about 1 weight percent of the composition, for increasing the surface adherence of the composition, (ii) behenylquaternary surfactant, in an amount between about 0.25 and about 7.5 weight percent of the composition; (iii) fatty alcohol, in an amount between about 0.75 and about 22.5 weight percent of the composition; and (iv) water, in an amount between about 40 and about 90 weight percent of the composition, to a surface to be shaved; and shaving the surface with a razor.

In one aspect, the ethoxylated fatty ester more preferably comprises between about 0.01 and about 0.05 weight percent of the composition, and most preferably between about 0.1 and about 0.2 weight percent of the composition. As discussed above, the ethoxylated fatty ester can comprise PEG 150 pentaerythrityl tetrastearate.

In one aspect, the fatty alcohol comprises between about 2.25 and about 6 weight percent of the composition, and most preferably comprises about 3.75 and about 5.25 weight percent of the composition. As discussed above, the fatty alcohol can comprise cetearyl alcohol.

The behenylquaternary surfactant can comprise a behentrimonium surfactant, in which case, the behenylquaternary surfactant is selected from the group consisting of behentrimonium methosulfate, behentrimonium chloride, behenalkonium chloride, dibehenyldimonium methosulfate or behenamidopropyl ethyldimonium ethosulfate.

The composition can further comprise organo-substituted polysiloxane, in an amount up to about 20 weight percent of the composition.

In one aspect, the organo-substituted polysiloxane is silicone. In this case, the silicone can comprise dimethicone.

As discussed above, we prefer that the composition be essentially free of salts of fatty acids.

In addition, the composition can further comprise titanium dioxide, in an amount between about 0.05 and about 5 weight percent of the composition.

In another embodiment of our invention, our method of shaving comprises: applying a shaving preparation composition comprising: (i) ethoxylated fatty ester, in the form of Formula (1) in an amount between about 0.01 and about 1 weight percent of the composition, for increasing the surface adherence of the composition, (ii) PEG 6 capric/caprylic triglycerides, in an amount between about 0.01 and about 1 weight percent of the composition, wherein the combined amount of the ethoxylated fatty ester and the PEG 6 capric/caprylic trigycerides is at most about 1.5 weight percent of the composition; (iii) behenylquaternary surfactant, in an amount between about 0.25 and about 7.5 weight percent of the composition; (iv) fatty alcohol, in an amount between about 0.75 and about 22.5 weight percent of the composition; and (v) water, in an amount between about 40 and about 90 weight percent of the composition, to a surface to be shaved; and shaving the surface with a razor.

In one aspect, it is more preferred that the PEG 6 capric/caprylic triglycerides be present in an amount between about 0.01 and about 0.5 weight percent of the composition. In another aspect, it most preferred the PEG 6 capric/caprylic triglycerides be present in an amount between about 0.05 and about 0.15 weight percent of the composition.

In yet another embodiment of our invention, our method of shaving comprises applying a shaving preparation composition comprising: (i) PEG 150 distearate, in an amount between about 0.01 and about 2 weight percent of the composition, for increasing the surface adherence of the composition; (ii) behenylquaternary surfactant, in an amount between about 0.25 and about 7.5 weight percent of the composition; (iii) fatty alcohol, in an amount between about 0.75 and about 22.5 weight percent of the composition; and (iv) water, in an amount between about 40 and about 90 weight percent of the composition, to a surface to be shaved; and shaving the surface with a razor.

In one aspect, it is more preferred that the PEG 150 distearate comprise between about 0.05 and about 0.5 weight percent of the composition. In another aspect, it is most preferred that the PEG 150 distearate comprise between about 0.1 and about 0.3 weight percent of the composition.

In still another embodiment of our invention, our method of shaving comprises applying a shaving preparation composition comprising: (i) PEG 6 capric/caprylic triglycerides, in an amount between about 0.01 and about 1 weight percent of the composition, for increasing the surface adherence of the composition; (ii) behenylquaternary surfactant, in an amount between about 0.25 and about 7.5 weight percent of the composition; (iii) fatty alcohol, in an amount between about 0.75 and about 22.5 weight percent of the composition; and (iv) water, in an amount between about 40 and about 90 weight percent of the composition, to a surface to be shaved; and shaving the surface with a razor.

In one aspect, it is more preferred that the PEG 6 capric/caprylic triglycerides comprise between about 0.05 and about 0.5 weight percent of the composition. In another aspect, it is most preferred that the PEG 6 capric/caprylic triglycerides comprise between about 0.05 and about 0.15 weight percent of the composition.

Our invention further includes a method for increasing the surface adherence of a soap-free, non-lathering shaving preparation. A preferred method comprises adding certain ethoxylated fatty esters, as described above, to a shaving preparation composition comprising behenylquaternary surfactant, fatty alcohol, and water. The resulting shaving preparation comprises the ethoxylated fatty esters, behenylquaternary surfactant, fatty alcohol, and water, in combinations and percent ranges as described above (i.e., the resulting shaving preparation comprises compositions in accordance with our invention).

In one embodiment of our invention, our method for increasing the surface adherence of a shaving preparation comprises: adding to a shaving preparation consisting essentially of behenylquaternary surfactant, fatty alcohol, and water, PEG 6 capric/caprylic triglycerides and ethoxylated fatty ester in the form of Formula (1), wherein the combined amount of the PEG 6 capric/caprylic triglycerides and the ethoxylated fatty ester is at most about 1.5 weight percent of the composition, and wherein after the adding step, the shaving preparation consists essentially of: (i) the behenylquaternary surfactant, in an amount between about 0.25 and about 7.5 weight percent of the preparation; (ii) the fatty alcohol, in an amount between about 0.75 and about 22.5 weight percent of the preparation; (iii) the water, in an amount between about 40 and about 90 weight percent of the preparation; (iv) the PEG 6 capric/caprylic triglycerides, in an amount between about 0.03 and about 1 weight percent of the preparation; and (v) the ethoxylated fatty ester, in an amount between about 0.05 and about 1 weight percent of the preparation, and wherein, after the adding step, the shaving preparation has a rinse off value of at least about 60 seconds.

In another embodiment of our invention, our method for increasing the surface adherence of a shaving preparation comprises: adding to a shaving preparation consisting essentially of behenylquaternary surfactant, fatty alcohol, and water, ethoxylated fatty ester in the form of Formula (1), wherein after the adding step, the shaving preparation consists essentially of: (i) the behenylquaternary surfactant, in an amount between about 0.25 and about 7.5 weight percent of the preparation; (ii) the fatty alcohol, in an amount between about 0.75 and about 22.5 weight percent of the preparation; (iii) the water, in an amount between about 40 and about 90 weight percent of the preparation; and (iv) the ethoxylated fatty ester, in an amount between about 0.04 and about 1 weight percent of the preparation, and wherein, after the adding step, the shaving preparation has a rinse off value of at least about 60 seconds.

In yet another embodiment of our invention, our method for increasing the surface adherence of a shaving preparation composition comprises: adding PEG 150 distearate to a shaving preparation consisting essentially of behenylquaternary surfactant, fatty alcohol, and water, wherein after the adding step, the shaving preparation consists essentially of: (i) the behenylquaternary surfactant, in an amount between about 0.25 and about 7.5 weight percent of the preparation; (ii) the fatty alcohol, in an amount between about 0.75 and about 22.5 weight percent of the preparation; (iii) the water, in an amount between about 40 and about 90 weight percent of the preparation; and (iv) the PEG 150 distearate, in an amount between about 0.01 and about 2 weight percent of the preparation, and wherein, after the adding step, the shaving preparation has a rinse off value of at least about 60 seconds.

In still another embodiment of our invention, our method for increasing the surface adherence of a shaving preparation composition comprises: adding PEG 6 capric/caprylic triglycerides to a shaving preparation consisting essentially of behenylquaternary surfactant, fatty alcohol, and water, wherein after the adding step, the shaving preparation consists essentially of: (i) the behenylquaternary surfactant, in an amount between about 0.25 and about 7.5 weight percent of the preparation; (ii) the fatty alcohol, in an amount between about 0.75 and about 22.5 weight percent of the preparation; (iii) the water, in an amount between about 40 and about 90 weight percent of the preparation; and (iv) the PEG 6 capric/caprylic triglycerides, in an amount between about 0.05 and about 1 weight percent of the preparation, and wherein, after the adding step, the shaving preparation has a rinse off value of at least about 60 seconds.

EXAMPLES

The trials set out in Tables 1A, 2A, 3A and 4A set forth below illustrate embodiments of our invention. All amounts are given in weight percent. The present invention is not limited to these examples.

TABLE 1A

| Component | Trials | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| CROTHIX Liquid (45% PEG 150 pentaerythrityl tetrastearate, 30% water, 25% PEG 6 capric/caprylic trigycerides) | 0 | 0.1 | 0.2 | 0.2 | 0.25 | 0.25 | 0.25 | 0.3 | 0.5 | 1 |
| INCROQUAT Behenyl TMS (25% | 5.5 | 5.5 | 5.5 | 5.5 | 5.5 | 5 | 5.5 | 5.5 | 5.5 | 5.5 |

TABLE 1A-continued

| Component | _____ Trials _____ | | | | | | | | | |
|---|---|---|---|---|---|---|---|---|---|---|
| | 1 | 2 | 3 | 4 | 5 | 6 | 7 | 8 | 9 | 10 |
| behentrimonium methosulfate, 75% cetearyl alcohol) | | | | | | | | | | |
| Water | 80.5 | 80.4 | 80.3 | 78.3 | 78.25 | 80.65 | 78.22 | 80.2 | 80 | 79.5 |
| Dimethicone | 8 | 8 | 8 | 8 | 8 | 6 | 8 | 8 | 8 | 8 |
| Isopropyl palmitate | 2 | 2 | 2 | 2 | 2 | 2 | 2 | 2 | 2 | 2 |
| Mineral oil | 2 | 2 | 2 | 2 | 2 | 2 | 2 | 2 | 2 | 2 |
| Titanium dioxide | 1.5 | 1.5 | 1.5 | 1.5 | 1.5 | 1 | 1.5 | 1.5 | 1.5 | 1.5 |
| Oxidized polyethylene beads | — | — | — | 1.5 | 1.5 | 2 | 1.5 | — | — | — |
| Methylparaben | 0.3 | 0.3 | 0.3 | 0.3 | 0.3 | — | 0.3 | 0.3 | 0.3 | 0.3 |
| Propylparaben | 0.1 | 0.1 | 0.1 | 0.1 | 0.1 | — | 0.1 | 0.1 | 0.1 | 0.1 |
| GERMABEN II-E (diazolidinyl urea and parabens preservative) | — | — | — | — | — | 1 | — | — | — | — |
| Vitamin E | 0.1 | 0.1 | 0.1 | 0.1 | 0.1 | 0.1 | 0.1 | 0.1 | 0.1 | 0.1 |
| Fragrance | — | — | — | 0.5 | 0.5 | — | 0.5 | — | — | — |
| Aloe vera powder | — | — | — | — | — | — | 0.03 | — | — | — |
| TOTAL: | 100 | 100 | 100 | 100 | 100 | 100 | 100 | 100 | 100 | 100 |

TABLE 2A

| Component | _____ Trials _____ | | | | | |
|---|---|---|---|---|---|---|
| | 1 | 2 | 3 | 4 | 5 | 6 |
| PEG 150 distearate | 0.25 | 0.1 | 0.5 | 1 | 1.5 | 2 |
| INCROQUAT Behenyl TMS (25% behentrimonium methosulfate, 75% cetearyl alcohol) | 5.5 | 5.5 | 5.5 | 5.5 | 5.5 | 5.5 |
| water | 78.25 | 80.4 | 78 | 77.5 | 77 | 78.5 |
| dimethicone | 8 | 8 | 8 | 8 | 8 | 8 |
| isopropyl palmitate | 2 | 2 | 2 | 2 | 2 | 2 |
| mineral oil | 2 | 2 | 2 | 2 | 2 | 2 |
| titanium dioxide | 1.5 | 1.5 | 1.5 | 1.5 | 1.5 | 1.5 |
| oxidized polyethylene beads | 1.5 | — | 1.5 | 1.5 | 1.5 | — |
| methylparaben | 0.3 | 0.3 | 0.3 | 0.3 | 0.3 | 0.3 |
| propylparaben | 0.1 | 0.1 | 0.1 | 0.1 | 0.1 | 0.1 |
| vitamin E | 0.1 | 0.1 | 0.1 | 0.1 | 0.1 | 0.1 |
| fragrance | 0.5 | — | 0.5 | 0.5 | 0.5 | — |
| TOTAL: | 100 | 100 | 100 | 100 | 100 | 100 |

TABLE 3A

| Component | Trial 1 |
|---|---|
| PEG 6 capric/caprylic triglycerides | 0.062 |
| INCROQUAT Behenyl TMS (25% behentrimonium methosulfate, 75% cetearyl alcohol) | 5.5 |
| water | 78.438 |
| dimethicone | 8 |
| isopropyl palmitate | 2 |
| mineral oil | 2 |
| titanium dioxide | 1.5 |
| oxidized polyethylene beads | 1.5 |
| methylparaben | 0.3 |
| propylparaben | 0.1 |
| vitamin E | 0.1 |
| fragrance | 0.5 |
| TOTAL: | 100 |

TABLE 4A

| Component | _____ Trials _____ | | | | |
|---|---|---|---|---|---|
| | 1 | 2 | 3 | 4 | 5 |
| CROTHIX Pastilles (100% PEG 150 pentaerythrityl tetrastearate) | 0 | 0.1 | 0.25 | 0.5 | 1 |
| INCROQUAT Behenyl | 5.5 | 5.5 | 5.5 | 5.5 | 5.5 |
| water | 80.5 | 80.4 | 80.25 | 80 | 79.5 |
| dimethicone | 8 | 8 | 8 | 8 | 8 |
| isopropyl palmitate | 2 | 2 | 2 | 2 | 2 |
| mineral oil | 2 | 2 | 2 | 2 | 2 |
| titanium dioxide | 1.5 | 1.5 | 1.5 | 1.5 | 1.5 |
| methylparaben | 0.3 | 0.3 | 0.3 | 0.3 | 0.3 |
| propylparaben | 0.1 | 0.1 | 0.1 | 0.1 | 0.1 |
| vitamin E | 0.1 | 0.1 | 0.1 | 0.1 | 0.1 |
| TOTAL: | 0 | 0.1 | 0.25 | 0.05 | 1 |

COMPARATIVE TESTING

We tested the rinse resistance of various embodiments of the present invention (the various trials set out in Tables 1A–4A) against a control and leading commercial shaving preparations (Comparative Samples 1, 2, 3), in accordance with the "Rinse Testing Procedure" set forth below. The control had a composition identical to Trial 6 in Table 1A minus the CROTHIX liquid, the difference being compensated for by a corresponding increase in the water component. The control yielded a rinse off value of 20 seconds, whereas, Comparative Samples 1, 2 and 3 yielded rinse off values of 10, 25 and 25 seconds, respectively. The results of the rinse testing of the trials set out in Tables 1A–4A are set out in Tables 1B to 4B below. Tables 1B to 4B illustrate that the trials illustrating various embodiments of the present invention exhibit exceptional rinse resistance. We believe that the embodiment of our invention containing PEG 6 capric/caprylic triglycerides exhibits exceptional rinse resistance which parallels the rinse resistance found in the other embodiments of the present invention.

Rinse Testing Procedure

The "Rinse Testing Procedure" is a test we developed to measure quantitatively the surface adherence ability of a substance in terms of a "rinse off value." A "rinse off value" is measured in seconds, and represents the time required to rinse away the substance from a glass surface.

The procedure requires the following supplies: hand held eyewash station modified with a 2 inch diameter shower spray head (472 openings in a concentric circle configuration) and a self-closing valve operated by a squeeze handle, connected to a reinforced PVC hose and plumbed to a temperature adjustable control (from Watersaver Faucet Co., Chicago, Ill.); about 100° F. unsoftened tap water; 3"×6"black-colored CARRARA® glass plates; an open design test tube rack; an adjustable test tube holder attached to a ring stand; a balance; a test tube brush; and a sink. Of course, equivalent supplies may be used in this procedure.

The glass plates should first be prepared by dispensing 2 grams of a 15% solution of sodium laureth sulfate (2EO) onto the plates, brushing the plates lightly with a test tube brush, rinsing the plates under running deionized water, and drying the plates with paper towels.

The shower head is set up as follows. The shower head is attached to the adjustable test tube holder attached to the ring stand, and the ring stand is placed on the edge of the sink. The shower head should be positioned so as to provide a water stream flowing downwards in a vertical direction. The test tube rack is placed in the sink directly under the shower head, so that a glass plate can be placed vertically and directly in the center of the water stream. The plate should be placed so that its vertical height is 6 inches. Further, the test tube rack should cover the bottom 2 inches of the glass plate. The shower head is then adjusted to a height of about 15–16 inches above the top of the glass plate. To ensure the same placement of the glass plate in the water stream, we prefer to use the corner of the sink to set up the shower head and the test tube rack.

The "Rinse Test Procedure" is then carried out as follows. The water source is turned on, and the flow rate is recorded. The water pressure should be high enough to provide a uniform flow rate of preferably about 85–95 g/sec the shower head is then turned on by depressing the squeeze handle. The water temperature is adjusted to about 100° F. On a glass plate, 1 g of a sample to be tested is weighed out and spread evenly in a 2" wide strip down the center of the plate (i.e., a 2"×6" vertical strip). The plate is then placed vertically in the test tube rack directly under the center of the water stream, and a timer (measuring seconds) is immediately started to measure the rinse off value of the sample. Upon complete rinsing off of the sample from the plate in the area not covered by the test tube rack (i.e., the 2"×4" upper portion of the sample strip), the timer is stopped. The time recorded is the rinse off value of the sample.

TABLE 1B

| Trials | Amount of CROTHIX Liquid Preparation | Rinses 1 | 2 | 3 | 4 | Average of Rinses |
| --- | --- | --- | --- | --- | --- | --- |
| 1 | 0 | 19 | 14 | 20 | — | 17.6 |
| 2 | 0.1 | 30 | 45 | 21 | — | 32 |
| 3 | 0.2 | 80 | 90 | 60 | — | 76.6 |
| 4 | 0.2 | 150 | — | — | — | 150 |
| 5a* | 0.25 | 174 | 76 | 129 | 168 | 136.75 |
| 5b* | 0.25 | 115 | 120 | 110 | 103 | 112 |
| 6 | 0.25 | 128 | — | — | — | 128.0 |
| 7 | 0.25 | 129 | 138 | 120 | 208 | 148.8 |
| 8 | 0.3 | 60 | 65 | 80 | — | 68.3 |
| 9 | 0.5 | 70 | 75 | 105 | — | 83.3 |
| 10 | 0.1 | 90 | 60 | 80 | — | 76.6 |

*Trial 5a values in Table 1B show rinse values from production. Trail 5b values show rinse values from a lab batch.

TABLE 2B

| Trials | Amount of PEG 150 distearate in Preparation | Rinses 1 | 2 | Average of Rinses |
| --- | --- | --- | --- | --- |
| 1 | 0.25 | 120 | 85 | 102.5 |
| 2 | 0.1 | 80 | 90 | 85 |
| 3 | 0.5 | 60 | 75 | 67.5 |
| 4 | 1 | 70 | 80 | 75 |
| 5 | 1.5 | 70 | 90 | 80 |
| 6 | 2 | 70 | 95 | 82.5 |

TABLE 3B

| Trial | Amount of PEG 6 capric/caprylic triglycerides | Rinse 1 |
| --- | --- | --- |
| 1 | 0.062 | 90 |

TABLE 4B

| Trial | Amount of CROTHIX Pastilles | Rinses 1 | 2 | 3 | Average of Rinses |
| --- | --- | --- | --- | --- | --- |
| 1 | 0 | 15 | 23 | 20 | 19 |
| 2 | 0.1 | 105 | 95 | 75 | 91.6 |
| 3 | 0.25 | 85 | 90 | 120 | 98.3 |
| 4 | 0.5 | 90 | 70 | 75 | 78.3 |
| 5 | 1 | 70 | 72 | 65 | 69 |

We also tested formulations of our invention on people according to the following protocol. A sequential monadic fully-labeled product test was conducted among a representative sample of 200 female wet-shavers who shave at least twice a week and who are 18 to 34 years of age. The panelists evaluated shave lotions with and without a surface adherence increasing compound of this invention. Each panelist was instructed to use each shave lotion at least 2 times per week within a 2 week period. Data was gathered by call-back interviews. The testers reported, among other things, that the formula with the surface adherence increasing compound of our invention provided excellent resistance to rinsing off from the skin and excellent adherence to wet skin.

INDUSTRIAL APPLICABILITY

The present invention provides compounds useful as shaving preparations that exhibit increased surface adherence. We envision that this invention can also be incorporated into other topical preparations, such as insect repellents, sun screens, and body washes, to improve their surface adherence.

While this invention has been described with respect to what is at present considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent formulations and functions.

We claim:

1. A method of shaving comprising:
    applying a shaving preparation composition comprising:
        (i) ethoxylated fatty ester, in an amount between about 0.01 and about 1 weight percent of the composition, for increasing the surface adherence of the composition, said ethoxylated fatty ester having the formula:

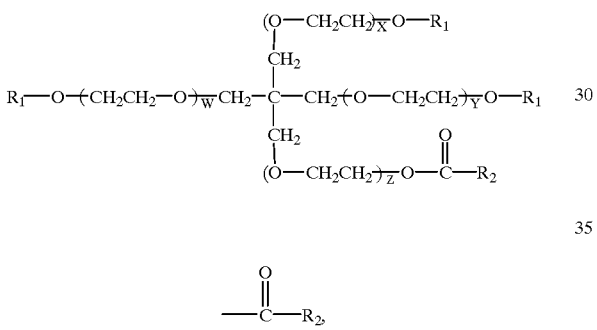

$R_2$ is a hydrocarbon chain having greater than 5 carbon atoms, and (W+X+Y+Z) is greater than 60;
        (ii) behenylquaternary surfactant, in an amount between about 0.25 and about 7.5 weight percent of the composition;
        (iii) fatty alcohol, in an amount between about 0.75 and about 22.5 weight percent of the composition; and
        (iv) water, in an amount between about 40 and about 90 weight percent of the composition, to a surface to be shaved; and
    shaving the surface with a razor.

2. The method of claim 1, wherein the ethoxylated fatty ester comprises between about 0.01 and about 0.5 weight percent of the composition.

3. The method of claim 1, wherein the ethoxylated fatty ester comprises between about 0.1 and about 0.2 weight percent of the composition.

4. The method of claim 1, wherein the ethoxylated fatty ester comprises PEG 150 pentaerythrityl tetrastearate.

5. The method of claim 1, wherein the fatty alcohol comprises between about 2.25 and about 6 weight percent of the composition.

6. The method of claim 1, wherein the fatty alcohol comprises between about 3.75 and about 5.25 weight percent of the composition.

7. The method of claim 1, wherein the fatty alcohol comprises cetearyl alcohol.

8. The method of claim 1, wherein the behenylquaternary surfactant comprises a behentrimonium surfactant.

9. The method of claim 1, wherein the behenylquaternary surfactant is selected from the group consisting of behentrimonium methosulfate, behentrimonium chloride, behenalkonium chloride, dibehenyldimonium methosulfate or behenamidopropyl ethyldimonium ethosulfate.

10. The method of claim 1, wherein the composition further comprises at least one of a polysiloxane containing an alkyl group and a polysiloxane containing an aryl group, in an amount up to about 20 weight percent of the composition.

11. The method of claim 1, wherein the composition further comprises a silicone, in an amount up to about 20 weight percent of the composition.

12. The method of claim 1, wherein the composition further comprises dimethicone, in an amount up to about 20 weight percent of the composition.

13. The method of claim 1, wherein the composition is essentially free of salts of fatty acids.

14. The method of claim 1, wherein the composition further comprises titanium dioxide, in an amount between about 0.05 and about 5 weight percent of the composition.

15. A method of shaving comprising:
    applying a shaving preparation composition comprising:
        (i) ethoxylated fatty ester, in an amount between about 0.01 and about 1 weight percent of the composition, for increasing the surface adherence of the composition, said ethoxylated fatty ester having the formula:

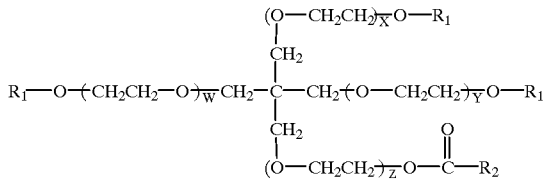

$R_2$ is a hydrocarbon chain having greater than 5 carbon atoms, and (W+X+Y+Z) is greater than 60;
        (ii) PEG 6 capric/caprylic triglycerides, in an amount between about 0.01 and about 1 weight percent of the composition, wherein the combined amount of said ethoxylated fatty ester and said PEG 6 capric/caprylic trigycerides is at most about 1.5 weight percent of the composition;
        (iii) behenylquaternary surfactant, in an amount between about 0.25 and about 7.5 weight percent of the composition;
        (iv) fatty alcohol, in an amount between about 0.75 and about 22.5 weight percent of the composition; and
        (v) water, in an amount between about 40 and about 90 weight percent of the composition, to a surface to be shaved; and
    shaving the surface with a razor.

16. The method of claim 15, wherein the PEG 6 capric/caprylic triglycerides is present in an amount between about 0.01 and about 0.5 weight percent of the composition.

17. The method of claim 15, wherein the PEG 6 capric/caprylic triglycerides is present in an amount between about 0.05 and about 0.15 weight percent of the composition.

18. A method of shaving comprising:
   applying a shaving preparation composition comprising:
   (i) PEG 150 distearate, in an amount between about 0.01 and about 2 weight percent of the composition, for increasing the surface adherence of the composition;
   (ii) behenylquaternary surfactant, in an amount between about 0.25 and about 7.5 weight percent of the composition;
   (iii) fatty alcohol, in an amount between about 0.75 and about 22.5 weight percent of the composition; and
   (iv) water, in an amount between about 40 and about 90 weight percent of the composition, to a surface to be shaved; and
   shaving the surface with a razor.

19. The method of claim 18, wherein the PEG 150 distearate comprises between about 0.05 and about 0.5 weight percent of the composition.

20. The method of claim 18, wherein the PEG 150 distearate comprises between about 0.1 and about 0.3 weight percent of the composition.

21. A method of shaving comprising:
   applying a shaving preparation composition comprising:
   (i) PEG 6 capric/caprylic triglycerides, in an amount between about 0.01 and about 1 weight percent of the composition, for increasing the surface adherence of the composition;
   (ii) behenylquaternary surfactant, in an amount between about 0.25 and about 7.5 weight percent of the composition;
   (iii) fatty alcohol, in an amount between about 0.75 and about 22.5 weight percent of the composition; and
   (iv) water, in an amount between about 40 and about 90 weight percent of the composition, to a surface to be shaved; and
   shaving the surface with a razor.

22. The method of claim 21, wherein the PEG 6 capric/caprylic triglycerides comprises between about 0.05 and about 0.5 weight percent of the composition.

23. The method of claim 21, wherein the PEG 6 capric/caprylic triglycerides comprises between about 0.05 and about 0.15 weight percent of the composition.

24. A method for increasing the surface adherence of a shaving preparation, said method comprising:
   adding to a shaving preparation consisting essentially of behenylquaternary surfactant, fatty alcohol, and water, PEG 6 capric/caprylic triglycerides and ethoxylated fatty ester having the formula:

$$R_1-O-(CH_2CH_2-O)_{\overline{W}}CH_2-C\begin{pmatrix}(O-CH_2CH_2)_{\overline{X}}O-R_1\\CH_2\\CH_2\\(O-CH_2CH_2)_{\overline{Z}}O-\overset{O}{\overset{\|}{C}}-R_2\end{pmatrix}-CH_2(O-CH_2CH_2)_{\overline{Y}}O-R_1$$

$$-\overset{O}{\overset{\|}{C}}-R_2,$$

$R_2$ is a hydrocarbon chain having greater than 5 carbon atoms, and $(W+X+Y+Z)$ is greater than 60, and the combined amount of said PEG 6 capric/caprylic triglycerides and said ethoxylated fatty ester is at most about 1.5 weight percent of the composition, and wherein after said adding step, the shaving preparation consists essentially of:
   (i) the behenylquaternary surfactant, in an amount between about 0.25 and about 7.5 weight percent of the preparation;
   (ii) the fatty alcohol, in an amount between about 0.75 and about 22.5 weight percent of the preparation;
   (iii) the water, in an amount between about 40 and about 90 weight percent of the preparation;
   (iv) the PEG 6 capric/caprylic triglycerides, in an amount between about 0.03 and about 1 weight percent of the preparation; and
   (v) the ethoxylated fatty ester, in an amount between about 0.05 and about 1 weight percent of the preparation,
   and wherein after said adding step the shaving preparation has a rinse off value of at least about 60 seconds.

25. A method for increasing the surface adherence of a shaving preparation, said method comprising:
   adding to a shaving preparation consisting essentially of behenylquaternary surfactant, fatty alcohol, and water, ethoxylated fatty ester having the formula:

$$R_1-O-(CH_2CH_2-O)_{\overline{W}}CH_2-C\begin{pmatrix}(O-CH_2CH_2)_{\overline{X}}O-R_1\\CH_2\\CH_2\\(O-CH_2CH_2)_{\overline{Z}}O-\overset{O}{\overset{\|}{C}}-R_2\end{pmatrix}-CH_2(O-CH_2CH_2)_{\overline{Y}}O-R_1$$

$$-\overset{O}{\overset{\|}{C}}-R_2,$$

$R_2$ is a hydrocarbon chain having greater than 5 carbon atoms, and $(W+X+Y+Z)$ is greater than 60, wherein after said adding step, the shaving preparation consists essentially of:
   (i) the behenylquaternary surfactant, in an amount between about 0.25 and about 7.5 weight percent of the preparation;
   (ii) the fatty alcohol, in an amount between about 0.75 and about 22.5 weight percent of the preparation;
   (iii) the water, in an amount between about 40 and about 90 weight percent of the preparation; and
   (iv) the ethoxylated fatty ester, in an amount between about 0.04 and about 1 weight percent of the preparation,
   and wherein after said adding step the shaving preparation has a rinse off value of at least about 60 seconds.

26. A method for increasing the surface adherence of a shaving preparation composition, said method comprising:
   adding PEG 150 distearate to a shaving preparation consisting essentially of behenylquaternary surfactant, fatty alcohol, and water, wherein after said adding step, the shaving preparation consists essentially of:
   (i) the behenylquaternary surfactant, in an amount between about 0.25 and about 7.5 weight percent of the preparation;
   (ii) the fatty alcohol, in an amount between about 0.75 and about 22.5 weight percent of the preparation;
   (iii) the water, in an amount between about 40 and about 90 weight percent of the preparation; and
   (iv) the PEG 150 distearate, in an amount between about 0.01 and about 2 weight percent of the preparation, and wherein after said adding step the shaving preparation has a rinse off value of at least about 60 seconds.

27. A method for increasing the surface adherence of a shaving preparation composition, said method comprising:
adding PEG 6 capric/caprylic triglycerides to a shaving preparation consisting essentially of behenylquaternary surfactant, fatty alcohol, and water, wherein after said adding step, the shaving preparation consists essentially of:
(i) the behenylquaternary surfactant, in an amount between about 0.25 and about 7.5 weight percent of the preparation;
(ii) the fatty alcohol, in an amount between about 0.75 and about 22.5 weight percent of the preparation;
(iii) the water, in an amount between about 40 and about 90 weight percent of the preparation; and
(iv) the PEG 6 capric/caprylic triglycerides, in an amount between about 0.05 and about 1 weight percent of the preparation,
and wherein after said adding step the shaving preparation has a rinse off value of at least about 60 seconds.

28. A shaving preparation composition that increases surface adherence to a surface to be shaved, the composition consisting essentially of:
ethoxylated fatty ester, in an amount between about 0.01 and about 1 weight percent of the composition, for increasing the surface adherence of the composition, said ethoxylated fatty ester having the formula:

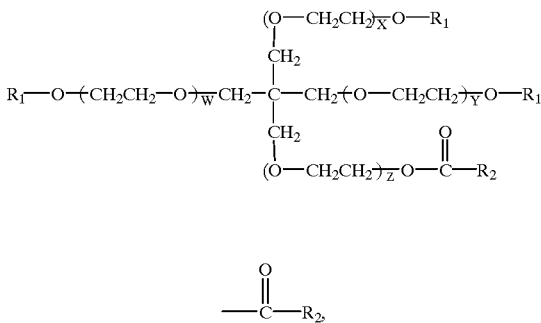

$R_2$ is a hydrocarbon chain having greater than 5 carbon atoms, and (W+X+Y+Z) is greater than 60;
behenylquaternary surfactant, in an amount between about 0.25 and about 7.5 weight percent of the composition;
fatty alcohol, in an amount between about 0.75 and about 22.5 weight percent of the composition; and
water, in an amount between about 40 and about 90 weight percent of the composition,
wherein the shaving preparation composition has a rinse off value from the surface to be shaved of at least about 60 seconds.

29. The composition of claim 28, wherein said ethoxylated fatty ester is present in an amount between about 0.01 and about 0.5 weight percent of the composition.

30. The composition of claim 28, wherein said ethoxylated fatty ester is present in an amount between about 0.1 and about 0.2 weight percent of the composition.

31. A shaving preparation composition that increases surface adherence, the composition consisting essentially of:
PEG 150 distearate, in an amount between about 0.01 and about 2 weight percent of the composition, for increasing the surface adherence of the composition;

behenylquaternary surfactant, in an amount between about 0.25 and about 7.5 weight percent of the composition;
fatty alcohol, in an amount between about 0.75 and about 22.5 weight percent of the composition; and
water, in an amount between about 40 and about 90 weight percent of the composition,
wherein the shaving preparation composition has a rinse off value from the surface to be shaved of at least about 60 seconds.

32. The composition of claim 31, wherein said PEG 150 distearate is present in an amount between about 0.05 and about 0.5 weight percent of the composition.

33. The composition of claim 31, wherein said PEG 150 distearate is present in an amount between about 0.1 and about 0.3 weight percent of the composition.

34. A shaving preparation composition that increases surface adherence, consisting essentially of:
PEG 6 capric/caprylic triglycerides, in an amount between about 0.01 and about 1 weight percent of the composition, for increasing the surface adherence of the composition;
behenylquaternary surfactant, in an amount between about 0.25 and about 7.5 weight percent of the composition;
fatty alcohol, in an amount between about 0.75 and about 22.5 weight percent of the composition; and
water, in an amount between about 40 and about 90 weight percent of the composition.

35. The composition of claim 34, wherein said PEG 6 capric/caprylic triglycerides is present in an amount between about 0.01 and about 0.5 weight percent of the composition.

36. The composition of claim 34, wherein said PEG 6 capric/caprylic triglycerides is present in an amount between about 0.05 and about 0.15 weight percent of the composition.

37. A shaving preparation composition that increases surface adherence, comprising:
PEG 6 capric/caprylic triglycerides, in an amount between about 0.01 and about 1 weight percent of the composition, and ethoxylated fatty ester, in an amount between about 0.01 and about 1 weight percent of the composition, for increasing the surface adherence of the composition, said ethoxylated fatty ester having the formula:

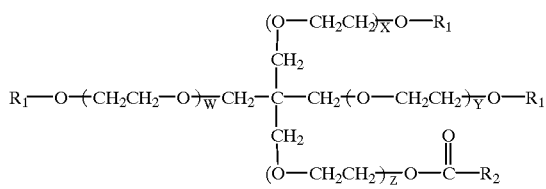

$R_2$ is a hydrocarbon chain having greater than 5 carbon atoms, and (W+X+Y+Z) is greater than 60, and wherein the combined amount of said PEG 6 capric/caprylic triglycerices and said ethoxylated fatty ester is at most about 1.5 weight percent of the composition;
behenylquaternary surfactant, in an amount between about 0.25 and about 7.5 weight percent of the composition;

fatty alcohol, in an amount between about 0.75 and about 22.5 weight percent of the composition; and water, in an amount between about 40 and about 90 weight percent of the composition.

38. The composition of claim 37, wherein said PEG 6 capric/caprylic triglycerides is present in an amount between about 0.05 and about 0.5 weight percent of the composition.

39. The composition of claim 37, wherein said PEG 6 capric/caprylic triglycerides is present in an amount between about 0.05 and about 0.15 weight percent of the composition.

40. The composition of claim 37, wherein said ethoxylated fatty ester is present in an amount between about 0.01 and about 0.5 weight percent of the composition.

41. The composition of claim 37, wherein said ethoxylated fatty ester is present in an amount between about 0.1 and about 0.2 weight percent of the composition.

42. The method of claim 1, wherein the composition further comprises at least one of methyl-substituted polysiloxane and phenyl-substituted polysiloxane, in an amount up to about 20 weight percent of the composition.

* * * * *

UNITED STATES PATENT AND TRADEMARK OFFICE
CERTIFICATE OF CORRECTION

PATENT NO.   : 6,024,951
DATED        : February 15, 2000
INVENTOR(S)  : Linda J. Babinski et al.

It is certified that error appears in the above-identified patent and that said Letters Patent is hereby corrected as shown below:

Column 2,
Lines 30-34, change "[-CO-$R_2$, $R_2$ is a hydrocarbon chain] to -- wherein $R_1$ us hydrogen or --CO-$R_2$, $R_2$ is a hydrocarbon chain.

Column 3,
Lines 24-28, change "[-CO-$R_2$, $R_2$ is a hydrocarbon chain] to -- wherein $R_1$ us hydrogen or --CO-$R_2$, $R_2$ is a hydrocarbon chain.

Claim 1, 15, 24, 25, 28, and 37,
Change "[-CO-$R_2$, $R_2$ is a hydrocarbon chain] to -- wherein $R_1$ us hydrogen or --CO-$R_2$, $R_2$ is a hydrocarbon chain.

Claim 28,
Line 5, change [1weight] to -- 1 weight --.

Signed and Sealed this

Eighteenth Day of December, 2001

Attest:

Attesting Officer

JAMES E. ROGAN
*Director of the United States Patent and Trademark Office*